United States Patent [19]

Kaplan

[11] Patent Number: 4,588,748
[45] Date of Patent: May 13, 1986

[54] THERAPEUTICALLY USEFUL BENZYLIDENE DERIVATIVES

[75] Inventor: Jean-Pierre Kaplan, Bourg-La-Reine, France

[73] Assignee: Synthelabo, Paris, France

[21] Appl. No.: 654,068

[22] Filed: Sep. 25, 1984

Related U.S. Application Data

[63] Continuation of Ser. No. 442,020, Nov. 16, 1982, abandoned.

[30] Foreign Application Priority Data

Nov. 18, 1981 [FR] France ............... 81 21559

[51] Int. Cl.$^4$ ............... C07C 103/29; A61K 31/165
[52] U.S. Cl. ............... 514/641; 514/507; 562/440; 564/107
[58] Field of Search ............... 562/440; 424/319; 564/171, 174, 107; 514/641, 507

[56] References Cited

U.S. PATENT DOCUMENTS

| | | | |
|---|---|---|---|
| 3,371,085 | 2/1968 | Reeder et al. | 562/440 |
| 3,429,878 | 2/1969 | Topliss | 562/440 |
| 4,010,154 | 3/1977 | Yamamoto et al. | 562/440 |
| 4,094,992 | 6/1978 | Kaplan et al. | 562/440 |

OTHER PUBLICATIONS

Kaplan et al., Chem. Abst., vol. 92, #67794 (1980).

*Primary Examiner*—James H. Reamer
*Attorney, Agent, or Firm*—Wegner & Bretschneider

[57] ABSTRACT

Benzylidene derivatives of the formula:

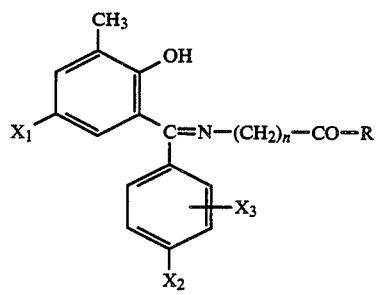

wherein n is 3, R represents an amino or hydroxy radical, or a group —OM in which M is an alkali metal, $X_1$ and $X_2$ are both Cl, and $X_3$ is hydrogen are new compounds possessing useful pharmacological properties; they are, more particularly, useful in the treatment of various diseases of the central nervous system.

5 Claims, No Drawings

THERAPEUTICALLY USEFUL BENZYLIDENE DERIVATIVES

CROSS REFERENCE TO RELATED APPLICATION

This application is a continuation of Ser. No. 442,020, filed Nov. 16, 1982 now abandoned.

DESCRIPTION

The present invention relates to new therapeutically useful benzylidene derivatives, to a process for their preparation and to pharmaceutical compositions containing them.

The benzylidene derivatives of the invention are those compounds of the general formula:

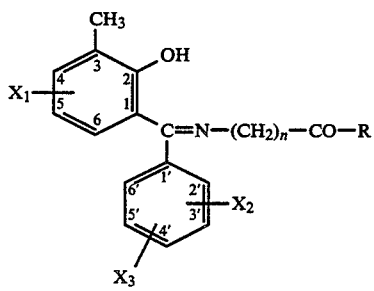

wherein n is an integer from 1 to 12, R represents an amino (—NH$_2$) or hydroxy radical, or a group —OM in which M is an alkali metal or alkaline earth metal and X$_1$, X$_2$ and X$_3$ each represent, independently of one another, a hydrogen atom, a halogen atom, the methoxy radical or a straight or branched-chain alkyl radical containing from 1 to 4 carbon atoms.

The preferred benzylidene derivatives of the invention are those which correspond to the general formula:

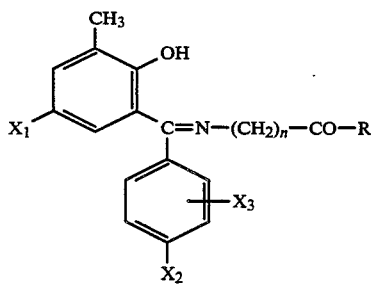

(wherein the various symbols are as hereinbefore defined) and, more particularly, those compounds wherein n represents an integer from 2 to 9 (preferably 2–4), X$_1$ represents a chlorine atom, a fluorine atom or the methyl radical, X$_2$ represents hydrogen, a chlorine atom, the methyl, ethyl, isopropyl or butyl radical or the methoxy radical, and X$_3$ represents a hydrogen atom or CH$_3$ in the 2' or 3' position.

Amongst such compounds, the preferred compounds are those in which n represents 3, R is as defined above (preferably NH$_2$), X$_1$ represents a chlorine atom or the methyl radical (preferably chlorine), X$_2$ represents a chlorine atom or the methyl radical (preferably chlorine), and X$_3$ represents hydrogen atom. It also is preferred that X$_1$ and X$_2$ each represent chlorine or each represent methyl. Compounds of outstanding importance are 4-{[(5-chloro-2-hydroxy-3-methylphenyl)-(4-chlorophenyl)-methylene]-amino}-butanoic acid,
4-{[(5-chloro-2-hydroxy-3-methylphenyl)-(4-chlorophenyl)-methylene]-amino}-butanamide,
3-{[(5-chloro-2-hydroxy-3-methylphenyl)-(4-chlorophenyl)-methylene]-amino}propanoic acid,
3-{[(5-chloro-2-hydroxy-3-methylphenyl)-(4-chlorophenyl)-methylene]-amino}-propanamide,
4-{[(5-chloro-2-hydroxy-3-methylphenyl)-(4-methylphenyl)-methylene]-amino}-butanamide and
4-{[(5-chloro-2-hydroxy-3-methylphenyl)-(4-methylphenyl)-methylene]amino}-butanoic acid, and alkali metal and alkaline earth metal salts of the aforesaid acids.

According to a feature of the invention, the benzylidene derivatives of general formula (I) are prepared by the process which comprises reacting a benzophenone of the general formula:

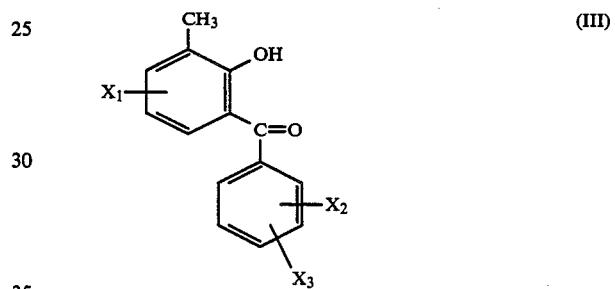

(wherein X$_1$, X$_2$ and X$_3$ are as hereinbefore defined) with a compound of the general formula:

$$H_2N-(CH_2)_n-CO-R \qquad (IV)$$

(wherein n and R are as hereinbefore defined), optionally in the form of an acid addition salt, such as the hydrochloride, at a temperature of from 20° to 120° C. in an organic solvent, such as methanol, ethanol or a methanol/toluene mixture, in the presence of a base.

The starting benzophenones of general formula (III) are new and can be prepared according to the following reaction scheme:

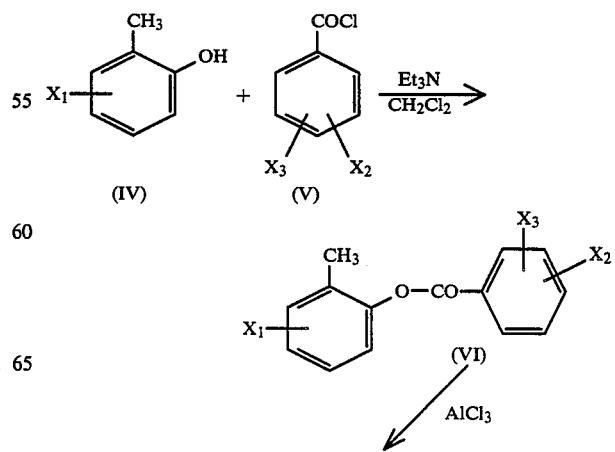

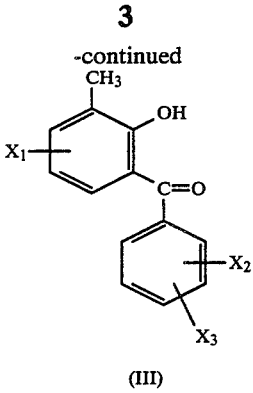

(III)

wherein $X_1$, $X_2$ and $X_3$ are as hereinbefore defined.

The following Examples illustrate the preparation of the benzylidene derivatives of general formula (I) of the present invention.

EXAMPLE 1

3-{[(5-Chloro-2-hydroxy-3-methylphenyl)-(4-chlorophenyl)-methylene]-amino}-propanoic acid [$X_1$=5-Cl, $X_2$=4-Cl, $X_3$=H, R=OH, n=2]

(A) (5-Chloro-2-hydroxy-3-methylphenyl)-(4-chlorophenyl)-methanone 13.6 g of 4-chloro-2-methylphenol and 15 g of 4-chlorobenzoyl chloride are reacted in 800 ml of methylene chloride, in the presence of 13 ml of triethylamine. This gives the intermediate of the formula:

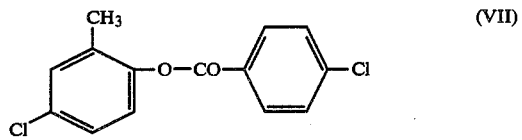

(VII)

which melts at 98°–99° C.

The latter is reacted with 20 g of aluminium chloride at 160° C.

This gives the desired ketone compound, melting at 41.2° C.

(B) (5-Chloro-2-hydroxy-3-methylphenyl)-(4-chlorophenyl)-methanone (98.4 g, 0.35 mol), sodium methoxide (19 g, 0.35 mol) and β-alanine (31.2 g, 0.35 mol) are added to 2 liters of toluene and 0.5 liters of methanol. The mixture is heated gradually and the ternary azeotrope (62° C.) is distilled. After a Dean-Stark apparatus has been fitted, the residue is heated at the reflux temperature of toluene for 6 hours. The mixture is then evaporated to dryness in vacuo. The solid residue is triturated with diethyl ether and filtered off. The solid is dissolved in 1.5 liters of water. The aqueous solution is acidified by the addition of citric acid to pH 4. The solid obtained is filtered off and then dissolved in CHCl$_3$. The chloroform solution is dried (MgSO$_4$) and then evaporated in vacuo. The solid obtained is triturated in petroleum ether, filtered off and dried. This gives the desired acid product, melting at 137.5°–138° C.

EXAMPLE 2

3-{[(5-Chloro-2-hydroxy-3-methylphenyl)-(4-chlorophenyl)-methylene]-amino}-propanamide [$X_1$=5-Cl, $X_2$=4-Cl, $X_3$=H, R=NH$_2$, n=2]

Under a hood, carbonyldiimidazole (5.56 g; 0.0312 mol) is added gradually to a stirred solution of the acid obtained in Example 1 (11 g; 0.0312 mol) in 150 ml of dry tetrahydrofuran. The stirring is continued for 1½ hours at ambient temperature, and the solution is then poured into 100 ml of liquid NH$_3$ and the whole is stirred until the evaporation of the ammonia has ended (about 3 hours). The residue is evaporated to dryness in vacuo. The residue is dissolved in CH$_2$Cl$_2$ and the methylene chloride solution is washed with water and with a saturated solution of sodium bicarbonate and then dried over MgSO$_4$. Evaporation gives a solid, which is chromatographed on a column (SiO$_2$, AcOEt). The solid obtained is recrystallised from AcOEt (i.e. ethyl acetate) to give a yellow solid.

Melting point of the product is 162°–163° C.

EXAMPLE 3

4-{[(5-Chloro-2-hydroxy-3-methylphenyl)-(4-chlorophenyl)-methylene]-amino}-butanamide [$X_1$=5-Cl, $X_2$=4-Cl, $X_3$=H, R=NH$_2$, n=3]

(5-Chloro-2-hydroxy-3-methylphenyl)-(4-chloropheny-methanone (4 g; 0.0142 mol) and then 200 ml of ethanol are added to a solution of 4-aminobutanamide hydrochloride (1.97 g; 0.0142 mol) and sodium methoxide (0.79 g; 0.0146 mol) in 500 ml of methanol. The mixture is evaporated to dryness. 600 ml of ethanol are added to the residue and the mixture is then evaporated to dryness again. The latter operation is repeated 5 times. The resulting solid is dissolved in CH$_2$Cl$_2$. The solution is washed with water, dried (MgSO$_4$) and filtered, and the filtrate is evaporated in vacuo. The oil obtained is crystallised from petroleum ether. The yellow crystals are filtered off, washed with diethyl ether and recrystallised from ethyl acetate after treatment with carbon black.

Melting point of the product is 155°–156° C.

EXAMPLE 4

4-{[(5-Chloro-2-hydroxy-3-methylphenyl)-(4-chlorophenyl)-methylene]-amino}-butanoic acid [$X_1$=5-Cl, $X_2$=4-Cl, $X_3$=H, R=OH, n=3]

4-Aminobutanoic acid (2.2 g; 0.0213 mol), sodium methoxide (1.16 g; 0.0213 mol) and (5-chloro-2-hydroxy-3-methylphenyl)-(4-chlorophenyl)-methanone (6 g; 0.0213 mol) are introduced into a mixture of 200 ml of ethanol and 400 ml of methanol, and the resulting mixture is then evaporated to dryness. Ethanol (500 ml) is added to the residue and the mixture is then evaporated to dryness. The latter operation is repeated 4 times. The residue is dissolved in 1 liter of water and the pH is acidified to pH 4 by the addition of citric acid. The precipitate is filtered off, washed with water and then dissolved in CH$_2$Cl$_2$. The organic solution is washed with water, dried (MgSO$_4$) and filtered, and the filtrate is evaporated to give an oil, which is crystallised once from petroleum ether and recrystallised twice from AcOEt.

Melting point of the product is 131°–132° C.

EXAMPLE 5

Sodium 4-{[(5-chloro-2-hydroxy-3-methylphenyl)-(4-chlorophenyl)-methylene]-amino}-butanoate [$X_1$=5-Cl, $X_2$=4-Cl, $X_3$=H, R=ONa, n=3]

A solution of sodium methoxide (11.68 ml; 0.748 N, 0.0087 mol) is added to a solution of the acid product of Example 4 (3.2 g; 0.0087 mol) in methanol (200 ml). The mixture is evaporated to dryness in vacuo at 30° C., 150 ml of diethyl ether are added and the mixture is evaporated to dryness again. The residue is taken up in diethyl ether and filtered off. The yellow solid is dried in a vacuum desiccator in the presence of $P_2O_5$.

Melting point of the product is greater than 240.

EXAMPLE 6

4-{[(5-Chloro-2-hydroxy-3-methylphenyl)-(4-ethylphenyl)-methylene]-amino}-butanoic acid and its sodium salt [$X_1$=5-Cl, $X_2$=4-$C_2H_5$, $X_3$=H, n=3, R=OH and ONa]

(A) (5-Chloro-2-hydroxy-3-methylphenyl)-(4-ethylphenyl)-methanone.

200 g (1.33 millimoles) of 4-ethylbenzoic acid are added rapidly to 500 ml of thionyl chloride with stirring. The mixture is heated at the reflux temperature for 4 hours. After evaporation of the $SOCl_2$ and distillation, 4-ethylbenzoyl chloride is obtained.

A solution of 50.6 g (0.3 mol) of 4-ethylbenzoyl chloride in 200 ml of diethyl ether is added dropwise to a solution of 42.8 g (0.3 mol) of 4-chloro-2-methylphenol and 30.4 g (0.3 mol) of triethylamine in 1 liter of diethyl ether.

After stirring for 4 hours at ambient temperature and standing overnight, 500 ml of water are added to the reaction mixture. After decantation, the organic phase is washed with 'carbonated' water and then with water and dried over $MgSO_4$.

After evaporation, a brown oil is obtained; the ester product is of the formula

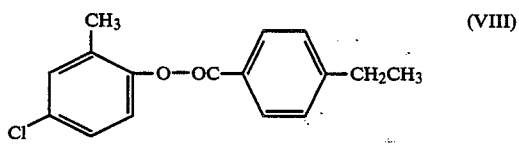

(VIII)

82 g (0.3 mol) of the obtained ester are introduced into a 500 ml Erlenmeyer flask and heated to 100° C. with stirring. 82 (0.615 mol) of aluminium chloride are added in portions and the temperature is then raised gradually to 180°–185° C. and kept there for 10 minutes.

After cooling the residue, liquid nitrogen is poured onto it so that the product can be crushed.

The ground residue is introduced into a stirred mixture of 200 ml of water, 200 g of ice and 20 ml of 12N hydrochloric acid. The product is extracted with methylene chloride and the methylene chloride solution is washed with water and dried over $MgSO_4$. The evaporated extract is purified on a column of Merck silica gel 40 with an 8/2 petroleum ether/methylene chloride mixture as the eluent. The product obtained melts at 152°–155° C.

(B) 4-{[(5-Chloro-2-hydroxy-3-methylphenyl)-(4-ethylphenyl)-methylene]-amino}-butanoic acid and its sodium salt.

0.84 g (0.0365 mol) of sodium is introduced into 500 ml of absolute ethanol. 3.75 g (0.0364 mol) of γ-aminobutyric acid and 10 g (0.0364 mol) of the benzophenone obtained above are added to the solution of sodium ethoxide. 300 ml of ethanol are slowly distilled off, 300 ml of absolute ethanol are then added and the same volume of ethanol is distilled again.

After evaporation, the residue is recrystallised from an 8/2 isopropanol/ethanol mixture.

After washing with diethyl ether and drying for 8 hours in vacuo at 100° C., the sodium salt is obtained.

Melting point=250° C. (dec.).

A sample of the sodium salt is dissolved in water. The solution is acidified to pH 4 with citric acid and then extracted with methylene chloride. After washing with water, drying over $MgSO_4$ and evaporation, the butanoic acid product crystallises on trituration in pentane.

Melting point of the acid is 121-2° C.

EXAMPLE 7

4-{[(5-Chloro-2-hydroxy-3-methylphenyl-(4-ethylphenyl)-methylene]-amino}-butanamide [$X_1$=5-Cl, $X_2$=4-$C_2H_5$, $X_3$=H, n=3, R=$NH_2$]

0.84 g (36.5 millimols) of sodium and 500 ml of absolute ethanol are introduced into a 1000 ml Erlenmeyer flask. When the reaction has ended, 5.05 g (36.4 millimols) of γ-aminobutyramide hydrochloride and then 10 g (36.4 millimols) of (5-chloro-2-hydroxy3-methylphenyl)-(4-ethylphenyl)-methanone are added.

300 ml of ethanol are slowly distilled slowly off, 300 ml of absolute alcohol are then added and the same volume is distilled again.

After evaporation to dryness, the residue is extracted with methylene chloride and the organic phase is washed with water and then dried over $MgSO_4$.

After evaporation, the residue is recrystallised from methanol. After washing with diethyl ether and drying for 8 hours in vacuo at 80° C., the amide product is obtained.

EXAMPLE 8

4-{[(5-Chloro-2-hydroxy-3-methylphenyl)-(4-isopropylphenyl)-methylene]-amino}-butanamide [$X_1$=5-Cl, $X_2$=4-$iC_3H_7$, $X_3$=H, n=3, R=$NH_2$.

(A) (5-Chloro-2-hydroxy-3-methylphenyl)-(4-isopropylphenyl)-methanone.

15.61 g (0.109 mol) of 4-chloro-2-methylphenol, 15.37 ml (0.109 mol) of triethylamine and 150 ml of $CH_2Cl_2$ are introduced into a 250 ml flat-bottomed flask. The mixture is heated to 40° C. and 20 g (0.109 mol) of 4-isopropylbenzoyl chloride are added dropwise. Boiling is continued for 8 hours. The mixture is evaporated to dryness, the residue is extracted with $CH_2Cl_2$ and the methylene chloride solution is washed with water, dried and evaporated. The residue is recrystallised from pentane. This gives white crystals, melting at 61°–62° C.

30 g (0.103 mol) of the compound of the formula

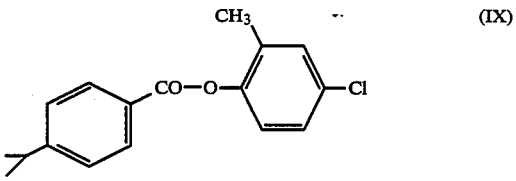

(IX)

are introduced into a wide-necked Erlenmeyer flask. The reaction mixture is heated to 90° C. with stirring, 30 g (0.224 mol) of $AlCl_3$ are added gradually and the mixture is then heated to 180° C. and kept at this temperature for 10 minutes. It is then allowed to cool to 50° C., 100 ml of liquid nitrogen are added and the mixture is stirred for 10 minutes. This gives a powder which is precipitated from a mixture of 200 g of ice and 100 ml of concentrated HCl. Extraction is carried out with CH₂Cl₂ and the methylene chloride solution is washed with water, dried and evaporated. The oil is filtered on silica in order to purify it. This gives a yellow oil ($n_D^{22.5}=1.619$).

(B) 4-{[(5-Chloro-2-hydroxy-3-methylphenyl)-(4-isopropylphenyl)-methylene]amino}-butanamide.

6 g (0.02 mol) of (5-chloro-2-hydroxy-3-methylphenyl)-(4-isopropylphenyl)-methanone, 3.86 g (0.031 mol) of γ-aminobutyramide hydrochloride, 5.61 ml of a 30% solution sodium methoxide in methanol, 100 ml of methanol and 200 ml of ethanol are introduced into a 500 ml flask.

This mixture is heated to 60° C. and then evaporated in vacuo. 300 ml of isopropanol are then added, the mixture is heated at the boiling point for 4 hours and then evaporated to dryness. The residue is washed with water and extracted with CH₂Cl₂, and the methylene chloride solution is washed with water, dried and evaporated. The residue is recrystallised from ethyl acetate.

Melting point of the product is 168°–169° C.

EXAMPLE 9

6-{[(5-Chloro-2-hydroxy-3-methylphenyl)-(4-chlorophenyl)-methylene]-amino}-hexanoic acid [$X_1=5$-Cl, $X_2=4$-Cl, $X_3=H$, R=OH, n=5]

42.17 g (0.15 mol) of (5-chloro-2-hydroxy-3-methylphenyl)-(4-chlorophenyl)-methanone, 8.1 g (0.15 mol) of sodium methoxide and 19.68 g (0.15 mol) of 6-aminohexanoic acid are introduced into a 1 liter flask.

400 ml of toluene and 100 ml of methanol are added, the mixture is heated gradually and the azeotrope formed is distilled, and the residue is then heated at the reflux temperature of the toluene for 6 hours, using a Dean-Stark apparatus.

The mixture is evaporated to dryness, the residue is triturated in diethyl ether and the solid is filtered off. The solid is introduced into water and the solution is acidified to pH 4 with citric acid. The resulting solid is filtered off and dissolved in chloroform, and the chloroform solution is dried over magnesium sulphate and evaporated. The compound is recrystallised from a cyclohexane/benzene mixture. The solid is redissolved in methylene chloride and the solution is passed over a silica column, elution being carried out with methylene chloride and then with an 80/20 methylene chloride/ethyl acetate mixture. After evaporation, a solid is obtained, which is dried.

Melting point of the product is 102.5°–103° C.

EXAMPLE 10

6-{[(5-Chloro-2-hydroxy-3-methylphenyl)-(4-chlorophenyl)-methylene]-amino}-hexanamide. [$X_1=5$-Cl, $X_2=4$-Cl, $X_3=H$, $R=NH_2$, n=5]

In an Erlenmeyer flask, 17.7 g (0.045 mol) of the acid obtained in Example 9 are introduced into 200 ml of tetrahydrofuran. 8 g (0.0495 mol) of carbonyldiimidazole are added in small amounts and the mixture is stirred for four hours at ambient temperature.

With cooling, the solution is saturated with ammonia and stirred for two hours. The mixture is evaporated to dryness, the residue is taken up in a mixture of water and chloroform, and the organic phase is decanted, washed with an aqueous solution of bicarbonate, dried over magnesium sulphate and evaporated. The compound obtained is recrystallised from a diisopropyl ether/ethyl acetate mixture.

Melting point of the amide product is 160°–161° C.

EXAMPLE 11

11-{[(5-Chloro-2-hydroxy-3-methylphenyl)-(4-chlorophenyl)-methylene]-amino}-undecanoic acid and its sodium salt [$X_1=5$-Cl, $X_2=4$-Cl, $X_3=H$, R=OH and ONa, n=10]0.83 g (36 millimols) of sodium and 500 ml of absolute ethanol are introduced into a 1000 ml Erlenmeyer flask filtered with a magnetic stirrer and a distillation head (or Dean-Stark apparatus).

When the reaction has ended, 7.17 g (35.6 millimols) of 11-aminoundecanoic acid and 10 g (35.6 millimols) of (5-chloro-2-hydroxy-3-methylphenyl)-4-chlorophenyl)-methanone are added.

300 ml of ethanol are slowly distilled off, the same volume of absolute ethanol is added and this operation is repeated.

After evaporation to dryness, the residue is dissolved in 200 ml of water, citric acid is added to pH 4 and the solution is then extracted with methylene chloride. The extract is washed with water and dried over MgSO₄ and, on evaporation, gives an uncrystallisable oil. The product is purified on a column of Merck silica gel 40 with a 9/1 methylene chloride diethyl ether mixture as the eluent, and recrystallised from cyclohexane.

Melting point of the obtained acid is 98°–99° C.

A solution of sodium methoxide is prepared by reacting 0.347 g (15.07 millimols) of sodium with 50 ml of pure methanol. This solution is added to a solution of 7 g (15.07 millimols) of the acid obtained as described above in 100 ml of pure methanol. After evaporation of the methanol, the residual sodium salt is recrystallised from a 9/1 isopropanol/ethanol mixture. After washing with diethyl ether and drying for 8 hours in vacuo at 100° C., the sodium salt of the acid is obtained.

Melting point of the salt is 255°–256° C. (dec.).

The following Table I shows by reference to general formula (I) the compounds of the invention which were prepared by way of examples.

TABLE I

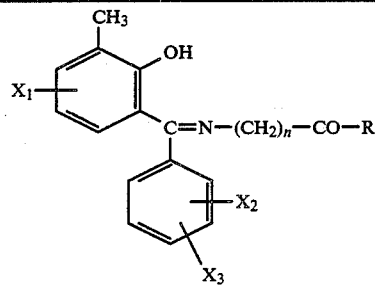

(I)

| Compound | n | $X_1$ | $X_2$ | $X_3$ | R | Melting point (°C.) |
|---|---|---|---|---|---|---|
| 1 | 3 | 5-Cl | H | 2-CH₃ | NH₂ | 140.6 |
| 2 | 3 | 5-Cl | H | 2-CH₃ | OH | 130.5 |
| 3 | 3 | 5-CH₃ | 5-CH₃ | 2-CH₃ | OH | 134.2 |
| 4 | 3 | 5-CH₃ | H | 2-CH₃ | NH₂ | 160.3 |
| 5 | 3 | 5-CH₃ | H | 2-CH₃ | OH | 128.7 |
| 6 | 3 | 5-CH₃ | 4-CH₃ | 2-CH₃ | NH₂ | 137.7 |
| 7 | 3 | 5-CH₃ | 5-CH₃ | 2-CH₃ | NH₂ | 112.7 |
| 8 | 3 | 5-CH₃ | H | 2-Br | OH | 105.2 |
| 9 | 3 | 5-CH₃ | H | 2-Br | NH₂ | 142 |
| 10 | 3 | 5-CH₃ | 4-CH₃ | 2-CH₃ | ONa | 165.4 |
| 11 | 3 | 5-Cl | 4-Cl | H | NH₂ | 155–156 |
| 12 | 3 | 5-Cl | 4-Cl | H | ONa | >240 |
| 13 | 3 | 5-Cl | 4-Cl | H | OH | 131–132 |
| 14 | 1 | 5-Cl | 4-Cl | H | NH₂ | 191–192 |
| 15 | 3 | 5-Cl | H | 2-Cl | OH | 102–103 |
| 16 | 3 | 5-Cl | H | 2-Cl | NH₂ | 135–136 |
| 17 | 3 | 5-Cl | 4-Cl | 2-CH₃ | NH₂ | 135–136 |

TABLE I-continued

Formula (I):

$$X_1 \text{—} \underset{\underset{\text{OH}}{|}}{\overset{\overset{CH_3}{|}}{\text{Ar}}} \text{—} C(\text{=}N\text{—}(CH_2)_n\text{—}CO\text{—}R)\text{—Ar}(X_2)(X_3)$$

| Compound | n | $X_1$ | $X_2$ | $X_3$ | R | Melting point (°C.) |
|---|---|---|---|---|---|---|
| 18 | 3 | 5-Cl | H | 2-Cl | ONa | >230 |
| 19 | 3 | 5-Cl | 4-Cl | 2-$CH_3$ | OH | 64–65 |
| 20 | 4 | 5-Cl | 4-Cl | H | OH | 110–111 |
| 21 | 2 | 5-Cl | 4-Cl | H | OH | 138–139 |
| 22 | 4 | 5-Cl | 4-Cl | H | $NH_2$ | 160–161 |
| 23 | 2 | 5-Cl | 4-Cl | H | $NH_2$ | 162–163 |
| 24 | 3 | 5-$CH_3$ | 4-Cl | H | $NH_2$ | 150.5–152.5 |
| 25 | 3 | 5-$CH_3$ | 4-$CH_3$ | H | $NH_2$ | 161–162 |
| 26 | 3 | 5-Cl | 4-$CH_3$ | H | $NH_2$ | 165–166 |
| 27 | 3 | 5-Cl | H | 3-Cl | $NH_2$ | 128–129 |
| 28 | 3 | 5-Cl | H | H | $NH_2$ | 160–161 |
| 29 | 3 | 5-$CH_3$ | 4-$CH_3$ | 3-$CH_3$ | $NH_2$ | 142 |
| 30 | 3 | 5-Cl | 4-$CH_3$ | 3-$CH_3$ | $NH_2$ | 151 |
| 31 | 1 | 5-Cl | 4-Cl | H | ONa | 258–259 |
| 32 | 1 | 5-Cl | 4-Cl | H | OH | 178–179 |
| 33 | 3 | 5-Cl | H | 3-$CH_3$ | $NH_2$ | 132–133 |
| 34 | 3 | 5-F | 4-Cl | H | $NH_2$ | 161–163 |
| 35 | 3 | 5-Cl | 4-$CH_3$ | H | $OCa/2$ | >245 |
| 36 | 3 | 5-Cl | 4-$CH_3$ | H | $OMg/2$ | 166–168 |
| 37 | 3 | 5-Cl | 4-$CH_3$ | H | ONa | 218–220 |
| 38 | 3 | 5-$CH_3$ | 4-$CH_3$ | H | $OCa/2$ | >240 (dec.) |
| 39 | 3 | 5-$CH_3$ | 4-$CH_3$ | H | ONa | 218–220 |
| 40 | 3 | 5-$CH_3$ | 4-Cl | 2-$CH_3$ | OH | 122–123 |
| 41 | 3 | 5-Cl | 4-$CH_3$ | 2-$CH_3$ | OH | 109–110 |
| 42 | 3 | 5-Cl | 4-$OCH_3$ | H | $NH_2$ | 178–179 |
| 43 | 3 | 5-Cl | 4-$C_2H_5$ | H | ONa | 250 (dec.) |
| 44 | 3 | 5-Cl | 4-$C_2H_5$ | H | $NH_2$ | 156–157 |
| 45 | 3 | 5-Cl | 4-$nC_4H_9$ | H | ONa | 241–243 |
| 46 | 3 | 5-Cl | 4-$nC_4H_9$ | H | $NH_2$ | 128–128.5 |
| 47 | 3 | 5-Cl | 4-$iC_3H_7$ | H | ONa | >260 |
| 48 | 3 | 5-Cl | 4-$iC_3H_7$ | H | $NH_2$ | 168–169 |
| 49 | 10 | 5-Cl | 4-Cl | H | ONa | 255–260 |
| 50 | 7 | 5-Cl | 4-Cl | H | ONa | 223–225 |
| 51 | 6 | 5-Cl | 4-Cl | H | ONa | 245–250 |
| 52 | 8 | 5-Cl | 4-Cl | H | ONa | 255–260 |
| 53 | 9 | 5-Cl | 4-Cl | H | ONa | 235–240 |
| 54 | 7 | 5-Cl | 4-Cl | H | $NH_2$ | 120.5–121 |
| 55 | 5 | 5-Cl | 4-Cl | H | $NH_2$ | 160–161 |
| 56 | 5 | 5-Cl | 4-Cl | H | OH | 102.5–103 |
| 57 | 5 | 5-Cl | 4-Cl | H | ONa | 230–232 |
| 58 | 5 | 5-Cl | 4-$CH_3$ | 2-$CH_3$ | $NH_2$ | 153–154 |
| 59 | 2 | 5-$CH_3$ | 4-$CH_3$ | 3-$CH_3$ | $NH_2$ | 179–180 |
| 60 | 2 | 5-Cl | 4-$CH_3$ | 3-$CH_3$ | $NH_2$ | 159–160 |
| 61 | 3 | 5-Cl | 4-Cl | H | $OCa/2$ | 255–257 |
| 62 | 3 | 5-Cl | 4-Cl | H | $OMg/2$ | 175 |
| 63 | 3 | 5-Cl | 4-$CH_3$ | H | OH | 135–136 |
| 64 | 3 | 5-$CH_3$ | 4-$CH_3$ | H | OH | 115–116 |
| 65 | 3 | 5-Cl | 4-$C_2H_5$ | H | OH | 121–122 |
| 66 | 3 | 5-Cl | 4-$nC_4H_9$ | H | OH | 112.5–113 |
| 67 | 3 | 5-Cl | 4-$iC_3H_7$ | H | OH | 108–109 |
| 68 | 10 | 5-Cl | 4-Cl | H | OH | 98–99 |
| 69 | 7 | 5-Cl | 4-Cl | H | OH | 108.5–109 |
| 70 | 6 | 5-Cl | 4-Cl | H | OH | 91–92 |
| 71 | 8 | 5-Cl | 4-Cl | H | OH | 69.5–70.5 |
| 72 | 9 | 5-Cl | 4-Cl | H | OH | 69–70 |
| 73 | 4 | 5-Cl | 4-Cl | H | ONa | >200 |
| 74 | 2 | 5-Cl | 4-Cl | H | ONa | >250 |

TABLE II

Starting benzophenones of the general formula (III):

$$X_1 \text{—} \underset{\underset{\text{OH}}{|}}{\overset{\overset{CH_3}{|}}{\text{Ar}}} \text{—} C(\text{=}O)\text{—Ar}(X_2)(X_3)$$

| Compound | $X_1$ | $X_2$ | $X_3$ | Melting point (°C.) |
|---|---|---|---|---|
| 1 | 5-Cl | H | 2-$CH_3$ | 38 |
| 2 | 5-$CH_3$ | 5-$CH_3$ | 2-$CH_3$ | liquid |
| 3 | 5-$CH_3$ | H | 2-$CH_3$ | liquid |
| 4 | 5-$CH_3$ | 4-$CH_3$ | 2-$CH_3$ | liquid |
| 5 | 5-$CH_3$ | H | 2-Br | 86.9 |
| 6 | 5-Cl | H | 4-Cl | 41–2 |
| 7 | 5-Cl | H | 2-Cl | 87–8 |
| 8 | 5-Cl | 4-Cl | 2-$CH_3$ | 53–4 |
| 9 | 5-$CH_3$ | H | 4-Cl | 45–6 |
| 10 | 5-$CH_3$ | H | 4-$CH_3$ | 55–6 |
| 11 | 5-Cl | H | 4-$CH_3$ | 76–7 |
| 12 | 5-Cl | H | 3-Cl | 130–1 |
| 13 | 5-$CH_3$ | 4-$CH_3$ | 3-$CH_3$ | 68 |
| 14 | 5-Cl | 4-$CH_3$ | 3-$CH_3$ | 108 |
| 15 | 5-Cl | H | 3-$CH_3$ | 108–9 |

The benzylidene derivatives of the invention were subjected to pharmacological experiments which demonstrated their action on the central nervous system.

The acute toxicity was determined on mice by intraperitoneal administration. The LD 50 (50% lethal dose), which causes the death of 50% of the animals, ranges from 250 to >1000 mg/kg.

The antidepressive action of the compounds was demonstrated by the antagonism towards the "head twitches" caused by L-5-hydroxytryptophan (L-5-HTP) in mice.

The mice (male, CD1 strain, Charles River France, body weight 18–22 g) receive increasing doses of the products to be studied, or the solvent, simultaneously with a dose of 250 mg/kg of L-5-HTP, by subcutaneous administration. Forty-five minutes after this injection of L-5-HTP, the number of "head twitches" is counted, for each mouse, for one minutes.

The average of the "head twitches", and also the percentage variation relative to the control batch, are calculated for each treatment.

From the effect-dose curve, the AD 50 (50% active dose, or dose which reduces the average number of "head twitches" by 50%) is determined by the graphical method of Miller and Tainter (1944).

The AD 50 of the compounds of the invention varies from 40 to 60 mg/kg, administered intraperitoneally.

The anticonvulsive action of the compounds was demonstrated by the antagonism towards the mortality induced in mice by bicuculline.

Bicuculline is a relatively selective blocker of postsynaptic GABA-ergic receptors and its convulsive and lethal effects are antagonised by compounds which increase the cerebral GABA level or which have a GABA-mimetic action.

The 50% active dose (AD 50) of the substances studied, namely the dose which protects 50% of the animals against the effect of bicuculline, was evaluated.

The AD 50 of the compounds of the invention varies from 10 to 100 mg/kg, administered intraperitoneally.

The compounds of the invention are active as antidepressants and anticonvulsants and also possess anxiolytic, analgesic and anti-inflammatory properties. They can be used in human and veterinary therapy for the treatment of various diseases of the central nervous system, for example for the treatment of depressions, psychoses and certain neurological diseases, such as epilepsy, spasticity and dyskinesia.

The invention consequently includes all pharmaceutical compositions containing the benzylidene derivatives of general formula (I) as active principles, in association with any excipients which are suitable for their administration, in particular their oral administration (tablets, coated tablets, gelatine capsules, capsules, cachets, and solutions or suspensions to be taken orally) or parenteral administration.

The daily dosage can range from 100 to 3000 mg.

I claim:

1. A compound of the formula:

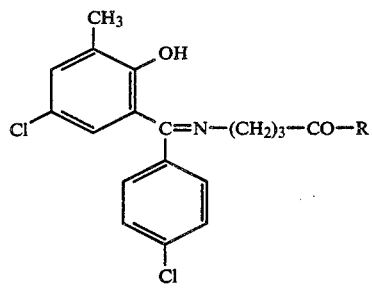

wherein R represents —$NH_2$, —OH or the group —OM in which M is an alkali metal or alkaline earth metal.

2. A compound according to claim 1, wherein R is $NH_2$.

3. An anticonvulsive composition comprising an anticonvulsive-effective amount of a compound according to claim 1 and a pharmaceutically acceptable carrier, excipient or adjuvant.

4. A method for treating convulsions, which comprises administering to a subject suffering from convulsions an effective amount of a compound according to claim 1.

5. A method of providing to a subject an anticonvulsive-effect which comprises orally administering to said subject an anticonvulsant effective amount of a compound of the formula

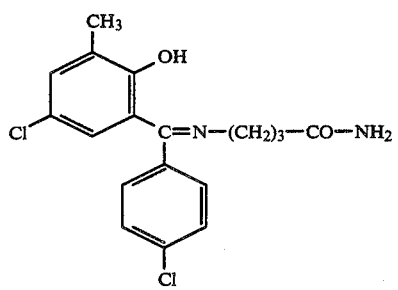

* * * * *